(12) United States Patent
Lal

(10) Patent No.: US 8,814,829 B2
(45) Date of Patent: Aug. 26, 2014

(54) DRUG DELIVERY DEVICE FOR FLUID RESTRICTED PATIENTS

(75) Inventor: Birendra K. Lal, Durham, NC (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 474 days.

(21) Appl. No.: 12/855,448

(22) Filed: Aug. 12, 2010

(65) Prior Publication Data

US 2012/0041416 A1 Feb. 16, 2012

(51) Int. Cl.
*A61M 37/00* (2006.01)
*A61M 5/14* (2006.01)
*A61M 39/22* (2006.01)

(52) U.S. Cl.
CPC *A61M 39/22* (2013.01); *A61M 5/14* (2013.01)
USPC .......................................................... 604/141

(58) Field of Classification Search
USPC .................. 604/187, 207–209, 141–144, 131
See application file for complete search history.

(56) References Cited

U.S. PATENT DOCUMENTS

| | | | |
|---|---|---|---|
| 2,507,214 A | 5/1950 | Medley | |
| 2,849,256 A | 8/1958 | Kowac | |
| 3,056,403 A | 10/1962 | Geweeke | |
| 3,153,414 A | 10/1964 | Beall et al. | |
| 3,872,879 A | 3/1975 | Green | |
| 3,900,022 A | 8/1975 | Widran | |
| 4,180,074 A | 12/1979 | Murry et al. | |
| 4,253,501 A | 3/1981 | Ogle | |
| 4,294,280 A | 10/1981 | Tom | |
| 4,314,560 A * | 2/1982 | Helfgott et al. | 606/171 |
| 4,391,599 A | 7/1983 | Jenkins | |
| 4,432,754 A | 2/1984 | Urqhart et al. | |
| 4,439,179 A | 3/1984 | Lueders et al. | |
| 4,474,574 A | 10/1984 | Wolfe et al. | |
| 4,525,156 A | 6/1985 | Benusa et al. | |
| 4,525,165 A | 6/1985 | Fischell | |
| 4,573,974 A | 3/1986 | Ruschke | |
| 4,588,394 A | 5/1986 | Schulte et al. | |
| 4,604,089 A | 8/1986 | Santangelo et al. | |
| 4,608,996 A | 9/1986 | Brown | |
| 4,613,325 A | 9/1986 | Abrams | |
| 4,648,668 A | 3/1987 | Hardwicki et al. | |
| 4,650,462 A | 3/1987 | DeSatnick et al. | |
| 4,655,197 A | 4/1987 | Atkinson | |
| 4,681,560 A | 7/1987 | Schulte et al. | |

(Continued)

FOREIGN PATENT DOCUMENTS

| | | |
|---|---|---|
| WO | WO86/03978 | 7/1986 |
| WO | WO87/00758 | 2/1987 |

(Continued)

*Primary Examiner* — Aarti B Berdichevsky
*Assistant Examiner* — Bradley Osinski
(74) *Attorney, Agent, or Firm* — K&L Gates LLP

(57) ABSTRACT

A syringe assembly for connecting to an intravenous ("IV") line includes: a syringe barrel having an actuation end and a discharge end; a syringe plunger moveable within the syringe barrel, the syringe plunger including a plunger head connected to a plunger arm; a seal between the plunger arm and the syringe barrel, the seal residing on an actuation end side of the syringe plunger; and a tube in fluid communication with the syringe barrel at a location between the seal and the plunger head, the tube having a distal end configured to be connected to the IV line.

17 Claims, 4 Drawing Sheets

(56) References Cited

U.S. PATENT DOCUMENTS

| | | | |
|---|---|---|---|
| 4,702,733 A | 10/1987 | Wright et al. | |
| 4,713,051 A | 12/1987 | Steppe et al. | |
| 4,714,462 A | 12/1987 | DiDomenico | |
| 4,784,582 A * | 11/1988 | Howseman, Jr. | 417/375 |
| 4,813,951 A | 3/1989 | Cannon | |
| 4,820,265 A | 4/1989 | DeSatnick et al. | |
| 4,832,685 A | 5/1989 | Haines | |
| 4,861,340 A * | 8/1989 | Smith et al. | 604/141 |
| 4,874,359 A | 10/1989 | White et al. | |
| 4,940,457 A | 7/1990 | Olson | |
| 5,002,528 A | 3/1991 | Palestrant | |
| 5,004,459 A | 4/1991 | Peabody et al. | |
| 5,011,477 A | 4/1991 | Winchell et al. | |
| 5,019,038 A | 5/1991 | Linden | |
| 5,053,002 A | 10/1991 | Barlow | |
| 5,053,031 A | 10/1991 | Borsanyi | |
| 5,059,182 A | 10/1991 | Laing | |
| 5,061,241 A | 10/1991 | Stephens, Jr. et al. | |
| 5,061,243 A | 10/1991 | Winchell et al. | |
| 5,074,334 A | 12/1991 | Onodera | |
| 5,074,443 A * | 12/1991 | Fujii et al. | 222/639 |
| 5,080,652 A | 1/1992 | Sancoff et al. | |
| 5,085,644 A | 2/1992 | Watson et al. | |
| 5,098,387 A | 3/1992 | Wiest et al. | |
| 5,137,529 A | 8/1992 | Watson et al. | |
| 5,152,746 A | 10/1992 | Atkinson et al. | |
| 5,152,753 A | 10/1992 | Laguette et al. | |
| 5,224,934 A | 7/1993 | Payne et al. | |
| 5,340,364 A | 8/1994 | Ghelli et al. | |
| 5,352,214 A | 10/1994 | Oscarsson | |
| 5,356,375 A | 10/1994 | Higley | |
| 5,356,379 A | 10/1994 | Vaillancourt | |
| 5,443,453 A | 8/1995 | Walker et al. | |
| 5,466,228 A | 11/1995 | Evans | |
| RE35,187 E | 3/1996 | Gortz | |
| 5,505,707 A | 4/1996 | Manzie et al. | |
| 5,607,418 A | 3/1997 | Arzbaecher | |
| 5,776,105 A | 7/1998 | Corn | |
| 5,807,312 A | 9/1998 | Dzwonkiewicz | |
| 5,810,783 A | 9/1998 | Claro | |
| 5,814,020 A | 9/1998 | Gross | |
| 5,871,478 A | 2/1999 | Berrigan | |
| 5,891,102 A | 4/1999 | Hiejima et al. | |
| 5,906,597 A | 5/1999 | McPhee | |
| 5,911,708 A | 6/1999 | Teirstein | |
| 6,045,533 A | 4/2000 | Kriesel et al. | |
| 6,059,747 A | 5/2000 | Bruggeman et al. | |
| 6,206,850 B1 | 3/2001 | O'Neil | |
| 6,213,972 B1 | 4/2001 | Butterfield et al. | |
| 6,213,981 B1 | 4/2001 | Hiejima et al. | |
| 6,471,686 B1 | 10/2002 | Berrigan | |
| 6,623,447 B2 | 9/2003 | Miles et al. | |
| 6,623,455 B2 | 9/2003 | Small et al. | |
| 6,702,779 B2 | 3/2004 | Connelly et al. | |
| 6,923,785 B2 | 8/2005 | Miles et al. | |
| 6,936,035 B2 | 8/2005 | Rake et al. | |
| 6,981,967 B2 | 1/2006 | Massengale et al. | |
| 7,018,360 B2 | 3/2006 | Flaherty et al. | |
| 7,018,375 B2 | 3/2006 | Berrigan | |
| 7,128,727 B2 | 10/2006 | Flaherty et al. | |
| 7,608,061 B2 | 10/2009 | Schinazi et al. | |
| 7,794,436 B2 | 9/2010 | Pinel | |
| 7,815,604 B2 | 10/2010 | Massengale et al. | |

FOREIGN PATENT DOCUMENTS

| | | |
|---|---|---|
| WO | WO87/06473 | 11/1987 |
| WO | WO91/08002 | 6/1991 |
| WO | WO93/00944 | 1/1993 |
| WO | WO93/10831 | 6/1993 |
| WO | WO95/04571 | 2/1995 |
| WO | WO98/15306 | 4/1998 |

* cited by examiner

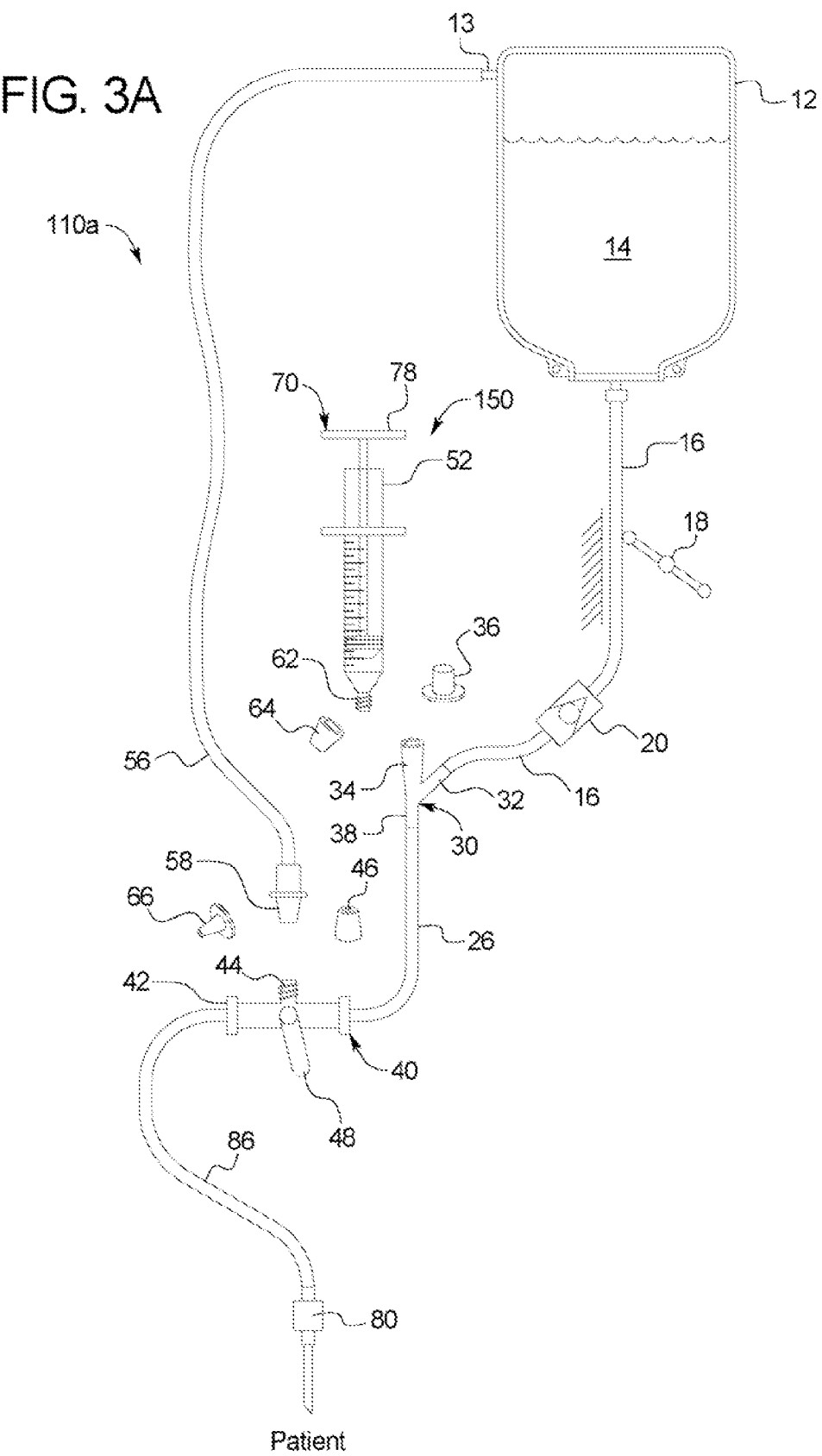

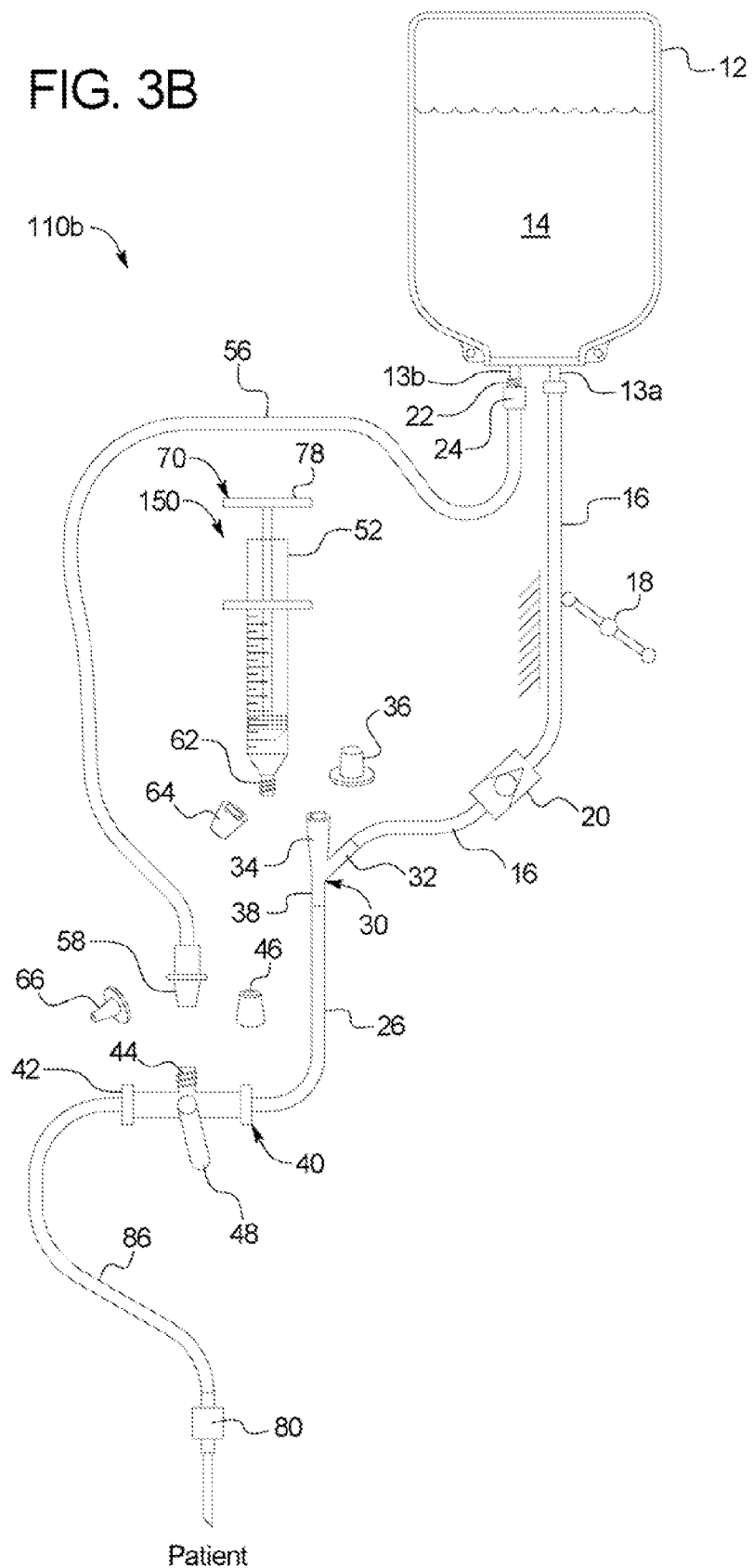

DRUG DELIVERY DEVICE FOR FLUID RESTRICTED PATIENTS

BACKGROUND

Certain drug infusion patients are considered flow restricted or volume restricted, meaning they can only receive a certain amount of medical fluid or drug over a given period of time. Neonatals or babies are one class of fluid restricted patients. Their bodies are too small to receive more than a certain amount of medical fluid or drug over a given infusion period.

There are circumstances in which a drug infusion patient, including fluid restricted patients, needs an infusion of a second drug or medical fluid in addition to the primary drug or medical fluid that the patient is currently receiving. In the situation in which the patient is fluid restricted, needing a second drug or medical fluid can present a problem if the primary drug or medical fluid that the patient is receiving is at or close to the maximum allowable flowrate for the patient.

In the above scenario, one solution is to inject the second drug or medical fluid into the primary fluid administration or intravenous ("IV") bag. Here, the second fluid mixed with the first fluid in the bag upstream of the pump or the gravity-feed tube such that the flowrate through the pump or the gravity-feed tube does not vary despite the fact that a portion of the flowrate now includes the second medical fluid or drug. There are a number of problems with this approach however. First and foremost is that the patient may need the entire dose of the medical fluid or drug quickly and does not have the time to wait for the bag of primary fluid to be delivered to receive the full dose.

The second problem is effectiveness. That is, even if the patient has the time to allow the second drug to be delivered from the primary IV bag, the second drug may not be effective if diluted in the primary IV bag. In addition, the drug may have a lower specific gravity than the primary drug or solution and thus may tend to be delivered last to the patient.

A solution to the above-described scenario is needed accordingly.

SUMMARY

The present disclosure sets forth an apparatus and method to address the above-stated scenario. The apparatus includes an administration or intravenous ("IV") line set and a syringe assembly that attaches to the IV line set. The IV line set extends from a bag or container holding a drug or medical fluid for infusion into the patient to a patient access device, e.g., catheter, cannula or needle for accessing the patients vascular system. The IV line may or may not operate with an infusion pump, such as an infusion pump provided by the assignee of the present disclosure.

The IV line includes a y-site located downstream of the IV bag and in one embodiment downstream of a section of the tubing that would operate with an infusion pump. The y-site provides a secondary access to the IV line. The y-site is provided in one embodiment with a check valve that prevents fluid from backflowing or traveling upstream to the IV bag. In an alternative embodiment, the check valve is provided for the same purpose, upstream of the y-site, between the y-site and the IV bag.

A multi-way valve or stopcock is located in the IV line downstream of the y-site, between the y-site and the patient access device. The valve in one embodiment includes a first, "normal flow" position in which fluid flows to the patient access device. The valve in a second, "secondary fluid" position instead flows fluid out a secondary fluid port. The valve optionally has a third position in which all fluid flow is stopped.

A syringe assembly is provided, which includes a tube is connected fluidly to an actuation end of a barrel of the syringe. The second fluid port of the multi-way valve is configured to connect, e.g., via a female or male luer connector, fluidly and sealingly with the tube of the syringe assembly, which can be provided with a male or female luer connector. The discharge end or outlet nozzle of the syringe is configured to connect fluidly and sealingly with a mating connector located at the free y-site administration port, which under normal flow conditions is capped.

The syringe head plunger is provided with a movable or slideable discharge or nozzle end seal to the inside of the syringe barrel. The barrel of the syringe is also fitted with a second, actuation end seal that is in one embodiment fixed. The discharge end and actuation end seals provide a sealed, variable volume within the syringe barrel.

In normal operation, the syringe assembly is not connected to the IV line. The free y-site administration port is capped. The multi-way valve or port is set to the normal flow position, so that fluid flows from the valve to the patient access device and not to the secondary fluid point of the multi-way valve.

When a fluid restricted patient needs a volume (e.g., small volume) of secondary medical fluid or drug, the syringe assembly is connected to the IV line to create a secondary closed-loop bypass. The discharge end or outlet nozzle of the syringe is connected fluidly and sealingly, e.g., threadingly, to the y-site administration port. The connector, e.g., male or female luer connector, located at the end of the tube extending from the syringe barrel is connected fluidly and sealingly to the mating connector, e.g., female or male luer connector, of the secondary port of the multi-way valve or stopcock.

To inject the secondary medical fluid or drug, the user sets the valve so the fluid does not flow to the patient access device and instead flows through the secondary port of the multi-way valve to the connected tube of the syringe assembly. When the user injects the secondary drug or medical fluid from the syringe to the IV line, the IV line between the y-site and the multi-way valve or stopcock fills with the secondary fluid. A like volume of the primary fluid is moved through the multi-way valve into the tube of the syringe assembly and potentially into the sealed expanding volume within the syringe barrel located behind the syringe plunger. Once a desired volume of the secondary fluid is delivered to the IV line, the multi-way valve is switched so that "normal" flow resumes but now with a volume of the secondary fluid or drug residing in the IV line.

The syringe assembly enables the secondary fluid or drug to replace a like volume of primary fluid instead of adding to the volume, resulting in an overall zero net total volume change. Also, the multi-way valve and y-site are located downstream of the IV bag, so that only the small volume of primary fluid left in the tubing downstream of the secondary fluid volume has to be delivered to the patient before the patient receives the secondary fluid or drug.

It is accordingly an advantage of the present disclosure to provide an improved intravenous administration system and method.

It is another advantage of the present disclosure to enable a secondary fluid or drug to be delivered effectively to a fluid restricted patient.

It is a further advantage of the present disclosure to enable a secondary fluid or drug to be delivered to a patient without increasing an overall volume of fluid delivered.

It is still another advantage of the present disclosure to provide a system and method for allowing a patient receiving a first medical fluid or drug to quickly and safely receive a second medical fluid or drug.

Additional features and advantages are described herein, and will be apparent from the following Detailed Description and the figures.

BRIEF DESCRIPTION OF THE FIGURES

FIGS. 3A and 3B are schematic elevation views of alternative embodiments for an IV administration set of the present disclosure.

DETAILED DESCRIPTION

Syringe Assembly Embodiment

Figure 1:
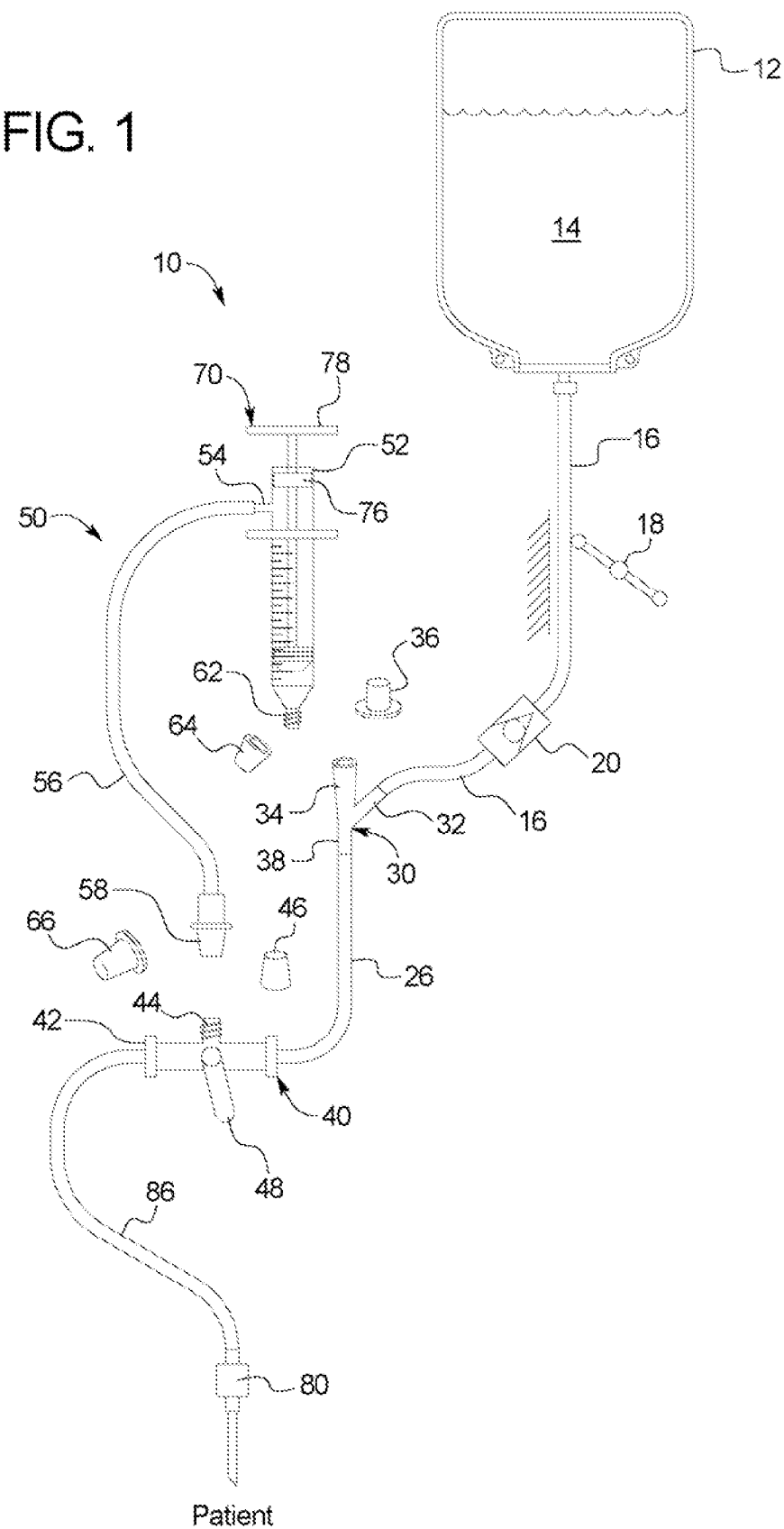
FIG. 1 is a schematic elevation view of one embodiment of an intravenous ("IV") administration set of the present disclosure.

Referring now to the drawings and in particular to FIG. 1, one embodiment of the intravenous ("IV") administration set and associated syringe assembly of the present disclosure is illustrated by IV administration set 10. Administration set 10 includes a supply container or bag 12, which holds a primary medical fluid/drug 14. As discussed herein, administration set 10 is particularly useful for a restricted flow patient, such as a baby or neonatal. Common primary medical fluids or drugs 14 for such patients include 0.9% NaCl or 5% dextrose solution, for example. Supply container 12 can be made of any suitable medical grade material, such as PVC.

Fluid leaving supply container 14 enters an upstream tubing section 16. Upstream tubing section 16 as well as any of the other tubing segments and associated connectors discussed herein are likewise made of a suitable medically accepted material, such as polyvinyl chloride ("PVC") or non-di(2-ethylhexyl)phthalate ("DEHP") materials. Upstream tubing section 16 is shown operating with an infusion pump 18, which can be a rotary or linear peristaltic pump. Alternatively, pump 18 can use a shuttle and platen, such as one provided by the COLLEAGUE™ infusion pump made by the assignee of the present disclosure. In an alternative embodiment, system 10 is gravity fed, such that infusion pump 18 is not used or needed.

In the illustrated embodiment, upstream tubing 16 includes or provides a check valve 20, which prevents medical fluid or drug 14 from flowing up tube 16 and back into supply container 12. Check valve 20 is provided alternatively with a y-site 30 connected to the end of upstream tubing 16.

Y-site 30 includes a main flow branch 32 and a secondary administration port 34. As illustrated, main flow branch 32 is connected to the distal end of upstream tubing 16. Administration port 34 includes a suitable connector, such as a female or male luer tip connector, which may be provided with a cap 36. Y-site 30 includes an outlet port 38, which is connected to a proximal end of an intermediate piece of tubing 26. The inlet fluid port 32 and outlet port 38 connect respectively to tubing sections 16 and 26 via a suitable tubing type connection, such as a barbed, glued, or press-fit tubing connection. The length and diameter of intermediate tubing 26 are sized in one embodiment so as to be able to receive the entire contents from a syringe barrel 52 of bypass syringe assembly 50.

A distal end of intermediate tubing section 26 connects via a suitable tubing type connection to a multi-way valve or stopcock 40. Multi-way valve 40 in an embodiment is a two-way valve. In an alternative embodiment, multi-way valve 40 can have an additional position in which flow through the valve is stopped completely. Multi-way valve 40 is provided with a primary fluid flow outlet 42 and a secondary fluid flow outlet 44. Secondary fluid flow outlet 44 can be a female or male luer connector. Secondary fluid flow outlet 44 may be capped via a suitable cap 46.

The user selects whether fluid flowing into valve 40 flows to main fluid outlet 42 or secondary fluid outlet 44 using a lever or other type of manually operated selector 48. When the user maneuvers selector 48 to a first position, fluid flows from intermediate tubing section 26, through multi-way valve 40 and its moving fluid outlet 42, through a downstream tubing section 86, to a patient access device 80, such as a catheter, cannula or needle. Alternatively, if the user maneuvers selector 48 to a second position, fluid flows instead from intermediate tubing section 26, through multi-way valve 40 and alternatively out secondary port and connector 44. Again, in one embodiment valve 40 includes a third position for selector 48, in which fluid entering valve 40 flows through neither outlet 42 nor outlet 44.

Patient access device 80, can be any suitable catheter, cannula or needle. Further, although not illustrated, any of tubing sections 16, 26 or 76 can operate with one or more line clamps, such as a Robert's type line clamp.

IV administration set 10 is operable with a syringe assembly 50, which includes a syringe 52 connected via a tubing connection port 54 to a bypass tube 56, which terminates at its distal end with a connector 58, such as a male or female luer connector, which is configured to mate with and connect to connector 44, e.g., a female or male luer connector, of multi-way valve 40.

Figure 2:
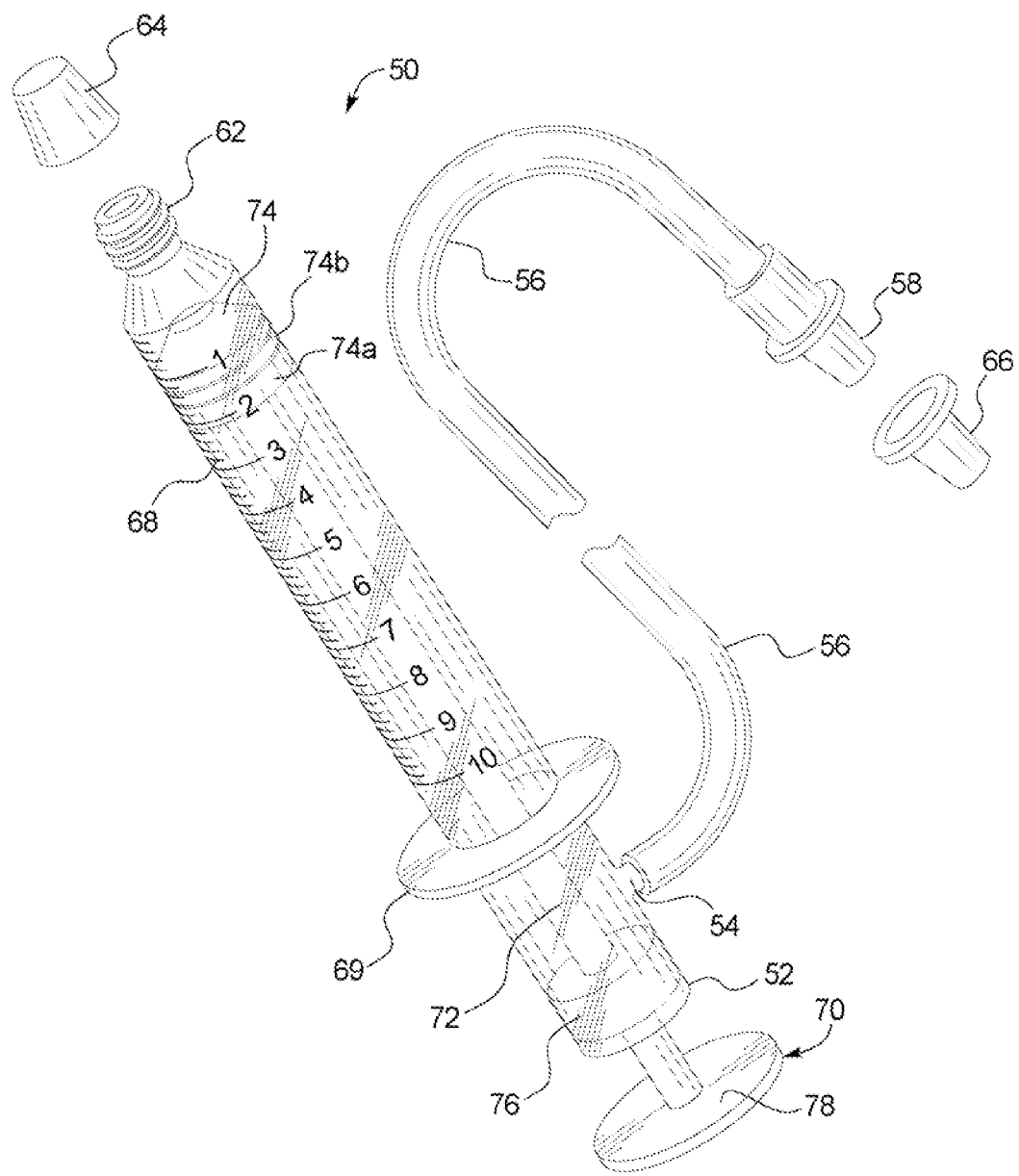
FIG. 2 is a schematic elevation view of one embodiment of a syringe assembly usable with the set of FIG. 1.

FIG. 2 shows syringe assembly 50 in more detail. Syringe barrel 52 includes a discharge end 62, which can be a male or female luer connector or luer lock that connects to secondary administration port 34 of y-site 30. A cap 64 is provided initially on discharge end 62 of syringe barrel 52. Likewise, a cap 66 is provided initially for covering distal port 58, e.g., a male or female luer connector, located at distal end of bypass tubing 56. Syringe barrel 52 also includes markings or indicia 68, that allow the user to fill syringe barrel 52 with a desired amount of the secondary medical fluid or drug. Examples of a secondary fluid/drug filled at syringe barrel 52 include antibiotics. Syringe barrel 52 further includes or defines a stationary flange 69 that the user can grasp to help push the secondary medical fluid/drug out discharge end 62 of syringe barrel 52.

As illustrated in FIG. 2, port 54 of syringe barrel 52 can be a hose barb or other type of compression connector for sealingly receiving the proximal end of bypass tubing 56. A plunger 70 is fitted inside syringe barrel 52. Plunger 70 includes a plunger arm 72, which is fitted at its discharge end with a plunger head 74. Plunger head 74 translates sealingly within syringe barrel 52, sealing to the inner wall of the syringe barrel. In an embodiment, ail outer wall 74a of plunger head 74 is made of a material that is compliant enough and sized appropriately, so as to seal directly to the inner wall of syringe barrel 52 in such a manner that plunger head 74 and plunger 70 can slide within syringe barrel 52. In an alterative embodiment, a separate o-ring 74b is fitted into a groove (not seen) provided in, plunger head 74 for sealing the plunger head to the inside wall of syringe barrel 52.

A second seal 76 is fitted at the actuation end of syringe barrel 52. Second seal 76 is in one embodiment formed with or otherwise fixedly secured to the inside wall of syringe barrel 52. Actuation end seal 76 creates a sliding seal with plunger arm 72. Seal 76 remains sealed to arm 72 as the user translates arm 72 back and forth via fixed flange 69 and plunger flange 78.

One actuation end seal 76 creates a sliding seal with plunger arm 72. Seal 76 remains sealed to arm 72 as the user translates arm 72 back and forth via flange 69 and plunger flange 78. Actuation end seal 76, o-ring 74b, and/or outer wall 74a in an embodiment are made of a medical grade compliant sealing material, such as closed-cell, silicone.

Administration end seal 76 is located closer to the administration end of syringe barrel 52 than is bypass port 54 of syringe barrel 52, so that administration end seal 76 and the seal made by plunger head 74 form a closed and sealed changing volume about the secondary fluid or bypass port 54 of syringe assembly 56. A plunger flange 78 is provided at the actuation end of plunger arm 72, so as to allow the user's thumb to press flange 78 while the user's fingers wrap about stationary flange 69 to allow the user to compress flange 78, plunger arm 72 and plunger head 74 into syringe barrel 52 to dispel the secondary medical fluid or drug through discharge outlet 62.

Method of Operation

To operate system 10 as it has been described in connection with FIGS. 1 and 2, under normal operation the extra connectors, e.g., luer connectors, are capped such that cap 46 caps luer connector 44, cap 66 caps luer connector 58, cap 64 caps luer connector 62 and cap 36 caps the luer connector of administration port 34. The user places selector 48 of multi-way valve 40 in a position that enables fluid flowing from supply container 12 to flow through tubing sections 16, 26 and 86, through patient access device 80 to the patient. Again, primary medical fluid/drug 14 can be pumped via pump 18 or gravity fed through the tubing and multi-way valve 40 to the patient.

When is it desired to give the patient a dose of a secondary fluid or drug, the user moves selector 48 into the position in which fluid flows instead out secondary port 44, or in an alternative embodiment moves selector 48 to a position in which no fluid flows out multi-way valve 40. The user removes cap 64 from discharge end 62 of syringe barrel 52, connects discharge end 62 to a vial or other container of the secondary medical fluid or drug (not illustrated) and pulls plunger 70 via plunger flange 78, such that a desired amount of the secondary medical fluid or drug enters syringe barrel 52 according to indicia 68 provided on the side of syringe barrel 52. The user then pulls cap 36 from administration port 34 of y-site 30 and connects connector 62 to the meeting connector at the administration port 34.

The user then removes caps 46 and 66 from connectors 44 and 58, respectively, and connects bypass tubing connector 58 to the mating valve connector 44. It should be appreciated that the connection sequence can be done differently than just described, e.g., by connecting syringe assembly 50 to valve 40 first, then connecting the assembly to y-site 30. In a further alternative embodiment, syringe assembly 50, with a pre-loaded syringe barrel 52, is pre-attached to y-site 30 and multi-way valve 40 prior to the administration of any primary medical fluid/drug 14 to the patient. It should be appreciated however that while system 10 requires tubing 16, 26 and 86 to be primed before delivery of primary fluid 14 to the patient, bypass line 56 and the sealed air volume in syringe barrel 52 between the plunger seal and actuation seal 76 of assembly 50 do not have to be primed. It may be desirable however to sterilize, e.g., via ethylene oxide, gamma radiation or steam sterilization, the inside of syringe assembly 50 prior to its use, in addition to sterilizing the remainder of IV administration set 10 prior to use.

Once syringe assembly 50 is connected fluidly to y-site 30 and multi-way valve 40, the user injects a desired amount of secondary medical fluid or drug from syringe barrel 52, through y-site administration port 34 and into intermediate tubing 26. Selector 48 of multi-way valve 40 is positioned such that primary medical fluid or drug residing in intermediate tubing 26 is pushed by the incoming secondary medical fluid or drug out secondary port 44 and into bypass tubing 56. If multi-way valve 40 has a totally off position and the user has forgotten to move selector 48 from the totally off position to the bypass position, the user will feel resistance at plunger flange 78, which will prompt the user to move selector 48 to the proper position. It should be appreciated that multi-way valve 40 can have suitable indicia informing the user of where to move selector 48 for normal flow, bypass flow and potentially no flow.

In an embodiment, the secondary medical fluid/drug delivered via syringe assembly 50 is delivered all at once, in a one-shot type of injection. Alternatively, it is possible to deliver fractions of the total volume of the secondary drug pulled into syringe barrel 52 at different points in time. In any case, the volume of secondary medical fluid or drug injected from syringe barrel 52 into intermediate line 26 moves a like volume of primary medical fluid or drug 14 through multi-way valve 40, bypass line 56 and if needed into the sealed air volume provided in syringe barrel 52. It may occur that some of the displaced primary fluid still resides in intermediate tube 26 and/or multi-way valve 40. This is unimportant, however, so long as there is enough volume in intermediate tube 26 to accept the entire volume of the secondary medical fluid or drug. That is, it is undesirable to push the secondary medical fluid or drug into bypass tube 56.

Once the volume of secondary medical fluid or drug is delivered to intermediate tubing 26, the user moves selector 48 to the position that allows IV flow to exit main flow outlet 42 and in turn prevents fluid from flowing out of secondary port connector 44 of multi-way valve 40. Normal flow then proceeds either by gravity or by infusion pump 18 action, but now with the segment of secondary medical fluid or drug located in intermediate tubing 26 flowing to the patient via access device 80 instead of a like volume of primary medical fluid or drug 14, which has instead been displayed into bypass tubing 56 in the previous step.

Three features of administration set 10 and the procedure just described should be noted. First, the overall volume of fluid delivered to the patient does not increase via the dose delivery of the secondary medical fluid or drug. Instead, as described, the secondary medical fluid or drug displaces and accordingly replaces a like amount of the primary medical fluid 14. Second, the entire volume of secondary medical fluid/drug is introduced at a point in the administration set 10 that is close to patient access device 80, such that the patient receives the entire volume of the secondary medical fluid or drug quickly after it is introduced into intermediate tubing section 26. Such delivery is desirable over the introduction of the secondary medical fluid or drug directly into solution container 12, which will dilute the secondary medical fluid/drug, in a worst case rendering the secondary drug ineffective, and in a best case slowing the injection of the secondary drug to the patient. Third, once connected the device maintains closed system efficacy.

It is contemplated to leave syringe assembly 50 connected to the remainder of IV administration set 10 until the delivery of primary medical fluid/drug 14 to the patient is completed.

Alternatively, syringe assembly 50 can be removed and y-site 30 and multi-way valve 40 recapped. In this second situation, the patient can receive multiple injections of one or more secondary medical fluid/drug at different times using different syringe assemblies 50 if needed.

Alternative Embodiments

Referring now to FIG. 3A, an alternative administration set 110a is illustrated. Administration set 110a is the same as administration set 10 in many respects and like element numbers are used where possible. With set 110a, however, bypass line 56 is connected to an additional port 13 extending from supply bag or container 12. The configuration of set 110a allows syringe 150 to be a standard syringe without an additional bypass port 54 and actuation and seal 76. It is contemplated here to pre-connect bypass line 56 to multi-way valve 40 and port 13 of solution bag 12. In this manner the entire assembly is sterilized via one of the methods discussed above prior to use. Bypass line 56 can be reused as many times as needed with one or more standard syringes 150 delivering one or more secondary medical fluid or drug as needed. It is also contemplated to eliminate the breakable connection between male or female luer 58 and female or male luer 44 and instead provide a permanent connection between multi-way valve 40 and bypass line 56.

The operation of alternative system 110a is in essence the same as the operation of IV administration set 10, except that bypass line 56 is presumably longer, which if needed compensates for the additional volume provided in the sealed area of syringe barrel 52 for IV administration set 10, which does not exist for alternative set 110a. The operation of multi-way pass valve 40 via selector 48 is the same as described above for IV administration set 10.

System 110b of FIG. 3B operates the same way as FIG. 3A. Here, however, port 13 of system 110a is moved to the position of injection port 13b, which is located adjacent to the administration port 13a connected to upstream tubing section 16. Injection port 13b includes a female or male luer connector 22, which connects removeably and sealingly to a mating male or female luer connector 24 located at the end of bypass tube 56. Connectors 22 and 24 can be capped initially. Tube 56 can also be clamped, removeably or permanently, near connector 24 to prevent primary fluid 14 from filling line 56 and to prevent air in line 56 from entering container 12.

In still another alternative embodiment (not illustrated) bypass tube 56 is replaced with the vial or container configured to connect removeably and sealingly to port 44 of multi-way valve 40 for collecting the displaced primary fluid 14 and air. The vial or container can have, if needed, a hydrophobic filter or membrane for allowing air to escape from the vial or container. In any of the alternative embodiments described herein, it is contemplated to sterilize the entire system with the bypass apparatus connected or disconnected (e.g., disconnected but held in the same packaging for sterilization).

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A syringe assembly for connecting to an intravenous ("IV") line comprising:

a syringe barrel having an actuation end portion and a discharge end;

a syringe plunger moveable within the syringe barrel, the syringe plunger including a plunger head affixed to a first end of a plunger rod, the plunger head forming a sliding seal engagement with an inner wall of the syringe barrel;

a seal sealing the actuation end portion of the syringe barrel, the seal forming a sliding seal engagement with the plunger rod;

wherein the syringe barrel, the syringe rod, the plunger head, and the seal are positioned and arranged to define a substantially hollow space extending from the seal to the plunger head; and a tube in fluid communication with the substantially hollow space at a location between the seal and the plunger head such that a fluid can flow from the tube into the substantially hollow space and contact the plunger head, the tube having a distal end that includes a medical fluid connector configured to be connected to the IV line.

2. The syringe assembly of claim 1, wherein the tube is connected to the syringe barrel near the seal.

3. The syringe assembly of claim 1, wherein the seal is fixed to the syringe barrel.

4. The syringe assembly of claim 1, wherein the discharge end of the syringe barrel is configured to attach sealingly to a connector of the IV line.

5. The syringe assembly of claim 1, wherein the medical fluid connector includes a luer connector configured to be mated to a second connector of the IV line.

6. The syringe assembly of claim 1, wherein the seal is a first seal, and wherein the plunger head includes a second seal that is moveably sealed to the syringe barrel.

7. The syringe assembly of claim 6, wherein the second seal is formed by an outer wall of the plunger head.

8. The syringe assembly of claim 6, wherein the second seal is an o-ring seal held by the plunger head.

9. The syringe assembly of claim 6, wherein the substantially hollow space forms an expandable sealed volume within the syringe barrel.

10. The syringe assembly of claim 1, wherein the tube is connected to a port extending from the syringe barrel.

11. The syringe assembly of claim 1, wherein the plunger head is configured to translate sealingly against the inner wall of the syringe barrel.

12. The syringe assembly of claim 1, wherein the IV line is configured to provide a primary medical fluid or drug to a patient, and the IV line is connected fluidly to at least one of: (i) a container for the primary medical fluid or drug, or (ii) a patient access device.

13. The syringe assembly of claim 12, wherein the tube is connected fluidly to the syringe and to a secondary connection of a multi-way valve, such that when the multi-way valve is set to a secondary flow position, a secondary medical fluid or drug injected from the syringe through an administration connection into the IV line causes a displacement of the primary medical fluid or drug into the substantially hollow space.

14. The syringe assembly of claim 13, wherein the multi-way valve includes a normal flow position that enables the primary medical fluid or drug and the secondary medical fluid or drug to flow to the patient.

15. The syringe assembly of claim 13, wherein a portion of the displaced primary medical fluid or drug is displaced into the substantially hollow space.

16. The syringe assembly of claim 13, wherein a volume of the primary medical fluid or drug displaced at least substantially matches a volume of the secondary medical fluid or drug injected from the syringe into the IV line.

17. A syringe assembly for connecting to an intravenous ("IV") line comprising:
   a syringe barrel having an actuation end portion and a discharge end;
   a syringe plunger moveable within the syringe barrel, the syringe plunger including a plunger head affixed to a first end of a plunger rod, the plunger head forming a sliding seal engagement with an inner wall of the syringe barrel;
   a seal sealing the actuation end portion the syringe barrel, the seal forming a sliding seal engagement with the plunger rod;
   wherein the syringe barrel, the syringe rod, the plunger head, and the seal are positioned and arranged to define a substantially hollow space extending from the seal to the plunger head; and
   a tube in medical fluid communication with the substantially hollow space at a location between the seal and the plunger head such that a medical fluid can flow from the tube into the substantially hollow space and contact the plunger head, the tube having a distal end configured to be connected to the IV line.

\* \* \* \* \*